United States Patent [19]

Boykin et al.

[11] Patent Number: 5,401,244
[45] Date of Patent: Mar. 28, 1995

[54] METHOD OF, AND STYLET APPARATUS FOR, INSTALLING A RETROGRADE CORONARY CANNULA

[75] Inventors: Christopher M. Boykin, Saline; Thomas T. Vaalburg, Ann Arbor, both of Mich.

[73] Assignee: Minnesota Mining and Manufacturing Company, St. Paul, Minn.

[21] Appl. No.: 238,416

[22] Filed: Apr. 28, 1994

Related U.S. Application Data

[63] Continuation of Ser. No. 979,010, Nov. 19, 1992, abandoned.

[51] Int. Cl.$^6$ .................... A61M 31/00; A61M 5/178; A61M 25/00
[52] U.S. Cl. ..................... 604/53; 604/170; 604/282
[58] Field of Search .............. 604/95, 170, 180, 280, 604/282, 264, 164–166, 49–53; 128/657, 772

[56] References Cited

U.S. PATENT DOCUMENTS

| Re. 32,306 | 12/1986 | Waters | 604/165 |
| 37,023 | 11/1862 | Woolley . | |
| D. 254,270 | 2/1980 | Ziegler | D24/23 |
| D. 309,014 | 7/1990 | Akerfeldt | D24/25 |
| D. 335,705 | 5/1993 | Buckberg et al. | D24/112 |
| D. 343,900 | 2/1994 | DeVries | D24/133 |
| D. 350,605 | 9/1994 | Williams | D24/133 |
| 2,164,926 | 7/1939 | Kleine . | |
| 2,393,003 | 1/1946 | Smith . | |
| 2,541,402 | 2/1951 | Caine . | |
| 2,571,207 | 10/1951 | Cox | 27/24 |
| 2,955,592 | 10/1960 | MacLean | 128/2 |
| 3,419,010 | 12/1968 | Williamson . | |
| 3,459,188 | 8/1969 | Roberts . | |
| 3,469,580 | 9/1969 | Huddy . | |
| 3,521,620 | 7/1970 | Cook . | |
| 3,547,119 | 12/1970 | Hall et al. . | |
| 3,628,524 | 12/1971 | Jamshida | 128/2 B |
| 3,630,198 | 12/1971 | Henkin | 604/170 |
| 3,653,388 | 4/1972 | Tenckhoff . | |
| 3,698,396 | 10/1972 | Katerndahl et al. . | |
| 3,726,269 | 4/1973 | Webster, Jr. | 128/2.05 |
| 3,757,768 | 9/1973 | Kline | 128/2 |
| 3,766,916 | 10/1973 | Moorehead et al. . | |
| 3,782,381 | 1/1974 | Winnie | 128/214.4 |
| 3,802,440 | 4/1974 | Salem et al. . | |
| 3,809,081 | 5/1974 | Loveless | 604/170 |
| 3,854,473 | 12/1974 | Matsuo | 128/8 |

(List continued on next page.)

FOREIGN PATENT DOCUMENTS

| 0141006 | 5/1985 | European Pat. Off. | A61M 25/00 |
| WO92/08510 | 5/1992 | WIPO | A61B 17/22 |

OTHER PUBLICATIONS

Pp. 12–14 from a price listing of Research Medical, Inc. for Retroplegia Retrograde Cardioplegia, undated.
Brochure entitled Retroplegia with Textured Balloon (2 pages) from Research Medical, Inc., undated.

(List continued on next page.)

Primary Examiner—John D. Yasko
Assistant Examiner—Adam J. Cermak
Attorney, Agent, or Firm—Gary L. Griswold; Walter N. Kirn; Stephen W. Bauer

[57] ABSTRACT

A coronary cannula and installation stylet set, the stylet having a shaft extending through the cannula of the coronary cannula to facilitate the installation of the cannula. The shaft has a stiff but resilient proximal portion and a deformable distal portion, shorter than the proximal portion, which can be deformed to hold the distal tip of the coronary cannula in a desired configuration to facilitate the insertion of the cannula into the coronary sinus. According to the method of this invention, the coronary cannula and installation stylet are provided, the distal tip of the coronary cannula is shaped by deforming the deformable distal portion of the stylet therein to facilitate its insertion into the coronary sinus. The tip of the coronary cannula is manipulated into the coronary sinus, and the stylet is removed from the coronary cannula once the coronary canula is in place in the coronary sinus.

21 Claims, 3 Drawing Sheets

U.S. PATENT DOCUMENTS

| | | | |
|---|---|---|---|
| 3,867,945 | 2/1975 | Long . | |
| 3,923,066 | 12/1975 | Francisoud et al. . | |
| 3,948,270 | 4/1976 | Hasson . | |
| 3,957,055 | 5/1976 | Linder et al. | 128/351 |
| 3,995,623 | 12/1976 | Blake et al. . | |
| 4,068,659 | 1/1978 | Moorehead | 128/214.4 |
| 4,068,660 | 1/1978 | Beck | 128/214.4 |
| 4,137,916 | 2/1979 | Killman et al. | 128/214.4 |
| 4,185,639 | 1/1980 | Linder | 128/200.26 |
| 4,273,131 | 6/1981 | Olsen . | |
| 4,351,334 | 9/1982 | Inglefield, Jr. | 128/218 |
| 4,351,341 | 9/1982 | Goldberg et al. | 128/348 |
| 4,400,168 | 8/1983 | Buechel et al. | 604/48 |
| 4,417,886 | 11/1983 | Frankhouser et al. | 604/53 |
| 4,456,017 | 6/1984 | Miles | 128/772 |
| 4,458,677 | 7/1984 | McCorkie, Jr. | 128/786 |
| 4,459,977 | 7/1984 | Pizon et al. . | |
| 4,469,109 | 9/1984 | Mehl | 128/753 |
| 4,504,268 | 3/1985 | Herlitze | 604/170 |
| 4,529,400 | 7/1985 | Scholten | 604/95 |
| 4,545,390 | 10/1985 | Leary | 128/772 |
| 4,559,041 | 12/1985 | Razi | 604/157 |
| 4,581,019 | 4/1986 | Curelaru et al. | 604/164 |
| 4,600,014 | 7/1986 | Beraha | 128/754 |
| 4,619,274 | 10/1986 | Morrison | 128/772 |
| 4,630,616 | 12/1986 | Tretinyak | 128/753 |
| 4,632,668 | 12/1986 | Wilson, Jr. et al. | 604/8 |
| 4,637,388 | 1/1987 | Melendy | 128/207.14 |
| 4,655,226 | 4/1987 | Lee | 128/754 |
| 4,676,249 | 6/1987 | Arenas et al. | 128/657 |
| 4,689,041 | 8/1987 | Corday et al. | 604/53 |
| 4,699,138 | 10/1987 | Behrstock | 128/207.16 |
| 4,699,140 | 10/1987 | Holmes et al. | 128/303 |
| 4,702,261 | 10/1987 | Cornell et al. | 128/754 |
| 4,713,049 | 12/1987 | Carter | 604/8 |
| 4,726,369 | 2/1988 | Mar | 128/303 |
| 4,743,265 | 5/1988 | Whitehouse et al. | 604/161 |
| 4,787,884 | 11/1988 | Goldberg | 604/8 |
| 4,790,825 | 12/1988 | Bernstein et al. | 604/170 |
| 4,793,363 | 12/1988 | Anoberman et al. | 128/754 |
| 4,808,158 | 2/1989 | Kreuzer et al. | 604/49 |
| 4,808,168 | 2/1989 | Warring | 604/158 |
| 4,834,709 | 5/1989 | Banning et al. | 604/170 |
| 4,838,282 | 6/1989 | Strasser et al. | 128/754 |
| 4,846,186 | 7/1989 | Box et al. | 128/657 |
| 4,863,430 | 9/1989 | Klyce et al. | 604/164 |
| 4,863,439 | 9/1989 | Sanderson | 604/264 |
| 4,886,067 | 12/1989 | Palermo | 128/657 |
| 4,888,000 | 12/1989 | McQuilkin et al. | 604/164 |
| 4,923,061 | 5/1990 | Trombley, III | 206/364 |
| 4,925,445 | 5/1990 | Sakamoto et al. | 604/95 |
| 4,927,412 | 5/1990 | Menasche | 604/96 |
| 4,976,688 | 12/1990 | Rosenblum | 604/95 |
| 5,001,825 | 3/1991 | Halpern | 29/456 |
| 5,007,434 | 4/1991 | Doyle et al. | 128/772 |
| 5,013,296 | 5/1991 | Buckberg et al. | 604/44 |
| 5,021,045 | 6/1991 | Buckberg et al. | 604/53 |
| 5,047,018 | 9/1991 | Gay et al. | 604/164 |
| 5,108,413 | 4/1992 | Moyers | 606/191 |
| 5,131,406 | 7/1992 | Kaltenbach | 128/772 |
| 5,161,534 | 11/1992 | Berthiaume | 128/657 |
| 5,163,912 | 11/1992 | Gay et al. | 604/164 |
| 5,169,397 | 12/1992 | Sakashita et al. | 606/27 |
| 5,176,647 | 1/1993 | Knoepfler | 604/158 |
| 5,188,630 | 2/1993 | Christoudias | 606/1 |
| 5,203,866 | 4/1993 | Islam | 606/186 |
| 5,226,427 | 7/1993 | Buckberg et al. | 128/772 |

OTHER PUBLICATIONS

Brochure entitled Retroplegia II—Coronary Sinus Cardioplegia Cannula with Retractaguard-Anti-retraction Lumen (2 pages) from Research Medical, Inc., undated.

Brochure entitled "Looking for a Retrograde Cardioplegia Cannula with a Manually-Inflated, Textured Silicone Balloon?" (1 page) from Research Medical, Inc., undated.

C. R. Bard, Inc. reference, dated at patent office Jan. 26, 1940.

Pp. 8 and 9 from Research Medical, Inc. Annual Report, undated.

Brochure entitled "Vent Catheters" from Research Medical, Inc., undated.

Brochure entitled "Instructions for Use: Retroplegia Cannula" of Research Medical, Inc., Nov. 25, 1991 undated.

One page of a brochure entitled "Retroplegia Coronary Sinue Perfusion Cannula" of Research Medical, Inc., undated.

Brochure entitled "Directions for Use: Retrograde Coronary Sinus Perfusion Cannula with Auto-Inflating-/Deflating Retention Cuff and Introducer" of DLP, Inc. dated Aug. 22, 1990.

Brochure entitled "Sarns—Sterilized Disposable Instruments" dated Apr. 1984.

(List continued on next page.)

OTHER PUBLICATIONS

One page flyer entitled "DLP Introduces the New Retrograde Coronary Sinus Perfusion Cannula," undated.

Retrograde pulmonary venous pressure measurement —Fact or artifact?; Buckberg; The Journal of Thoracic and Cardiovascular Surgery; vol. 59, No. 3, Mar. 1970; pp. 393–400.

Charles P. Bailey, M.D. et al., Cardiac Surgery, F. A. Davis Company, Philadephia, Pa, 1960, pp. 50-52, 75-77.

Gumersindo Blanco, M.D. et al., "A Direct Experimental Approach to the Aortic Valve II. Acute Retroperfusion of the Coronary Sinus", from the Department of Surgery and the Experimental Surgery Laboratory, School of Medicine, University of Puerto Rico, San Juan, Purerto Rico, Nov. 1955, pp. 171-177.

Edward P. Fitch, M.D. et al., "Obturators for Extracorporeal Circulation Cannulae"; OJ. Thoracic Surg., vol. 37, No. 5, Sep. 2, 1958, pp. 663-664.

"Sarns Presterilized Atrial Vent Catheter and Left Vent Catheter", The Annals of Thoracic Surgery, vol. 19, No. 3, Mar. 1975.

Brochure "Catheters and Related Products" by American Cystoscope Makers, Inc., p. 2558 (undated).

"Catheter Fittings and Accessories", Cardiovascular Catheters and Accessories, by United States Catheter and Instrument Corporation, New York, 1967-1968, p. 41.

"Mayo Coronary Perfusion Components (Balloon Style)" (date and source unknown).

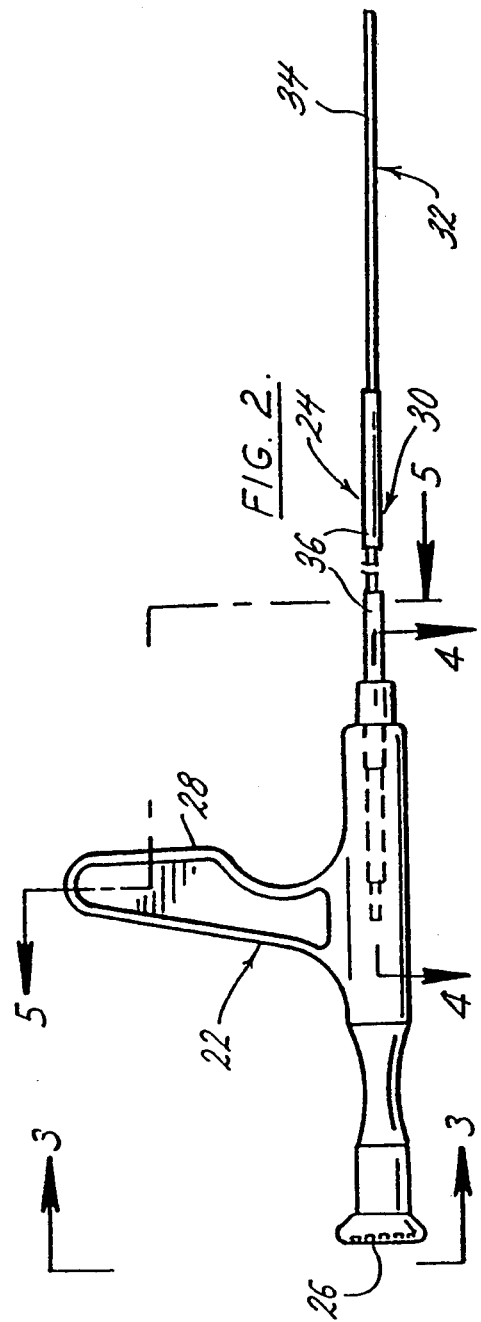

METHOD OF, AND STYLET APPARATUS FOR, INSTALLING A RETROGRADE CORONARY CANNULA

This is a continuation of application Ser. No. 07/979,010, filed Nov. 19, 1992, (now abandoned).

BACKGROUND AND SUMMARY OF THE INVENTION

This invention relates to a method of, and a stylet apparatus for, installing a retrograde coronary cannula.

Cardioplegia is a commonly used technique for protecting the heart during heart surgery in which a cooled cardioplegia solution, for example a potassium solution, is circulated through the heart. The cardioplegia solution stops the heart and reduces its temperature to minimize damage to the heart. Cardioplegia is often administered through the aorta in the antegrade direction, i.e., the direction of normal blood flow. However, there is increasing interest in administering cardioplegia in the retrograde direction, i.e., opposite the direction of normal blood flow. Retrograde administration of cardioplegia has been used in patients having critical coronary artery stenosis that would have made the antegrade administration of cardioplegia difficult and inefficient, and with patients suffering from aortal valve disease. A retrograde sinus catheter particularly adapted for the retrograde administration of cardioplegia is disclosed in U.S. patent application Ser. No. 07/874,589, filed Apr. 27, 1992, incorporated herein by reference.

There are two principle techniques for installing a coronary cannula in the coronary sinus for the administration of cardioplegia. The first is known as the "open atrium" technique in which the right atrium of the heart is substantially opened with a large incision so that direct access is provided to the coronary sinus. A disadvantage of this technique is that it makes it more difficult to drain venous blood from the vena cava and to drain blood from the right atrium. An alternative is to use a "blind" procedure in which only a small incision is made to gain access to the right atrium and the coronary sinus. It can be very difficult to manipulate the coronary cannula, which is typically small and flexible, into the proper position in the coronary sinus through this small puncture.

Generally, the method of installing a coronary cannula according to this invention comprises providing a coronary cannula with a stylet extending through the lumen of the cannula. The stylet has a handle and a shaft that extends through the lumen with a stiff but flexible proximal portion, and a deformable distal portion. The shaft is sufficiently long that the deformable distal portion extends generally to the tip of the coronary cannula. The tip of the coronary cannula is then shaped by deforming the deformable distal portion of the stylet inside the lumen to facilitate its insertion through an incision in the right atrium and into the coronary sinus. The tip of the coronary cannula is then manipulated into the coronary sinus by steering the shaped tip by manipulating the handle. After the tip of the coronary cannula is in place, the cannula is anchored, for example by inflating a balloon at the tip of the cannula provided for that purpose, and the stylet can be drawn from the lumen of the coronary cannula.

Generally, the stylet apparatus for installing a coronary cannula according to this invention is adapted to fit inside the lumen of a coronary cannula to facilitate the installation of the cannula into the coronary sinus. The stylet comprises a handle, and a shaft extending from the handle and adapted to fit inside the lumen of the cannula. The shaft comprises a stiff but resilient proximal portion and a deformable distal portion that can be permanently deformed to a desired shape when inside the cannula to hold the tip of the cannula in a preselected shape to facilitate the insertion of the cannula into the coronary sinus. In the preferred embodiment the shaft comprises a malleable steel wire and a tube surrounding the proximal portion of the wire, stiffening the proximal portion of the shaft while leaving the distal portion of the wire uncovered. The deformable distal portion of the stylet is shorter than the stiffer proximal portion so that the deformability of the distal portion does not interfere with the steering of the tip, as described below. The distal portion of the stylet may be colored so that the surgeon can gauge the depth of penetration of the stylet and cannula in order to facilitate proper placement of the cannula.

The coronary cannula is preferably provided with the stylet already in the lumen, although they could be provided separately, and the stylet inserted into the lumen before the installation of the cannula. With the stylet inside the lumen of the coronary cannula, the tip of the coronary cannula can be configured to pass readily through an incision in the right atrium and into the coronary sinus. The malleable distal portion of the stylet holds the tip of the cannula in the desired preformed configuration, while the stiffer, flexible proximal portion of the stylet allows the cannula to flex and bend sufficiently as the tip of the cannula is manipulated into the coronary sinus.

The method of installing the coronary cannula and the stylet apparatus for installing the cannula allow the cannula to be quickly inserted into the coronary sinus for the prompt administration of cardioplegia solution. The stylet apparatus also helps the surgeon gauge the depth of the tip to facilitate proper placement. The method and apparatus provide for the accurate placement of the cannula, and hold the cannula in place until it is anchored, for example by inflating a balloon on the cannula.

These and other features and advantages will be in part apparent, and in part pointed out, hereinafter.

BRIEF DESCRIPTION OF THE DRAWINGS

FIG. 2 is a partial side elevation view of the stylet;

Corresponding reference numerals indicate corresponding parts throughout the several views of the drawings.

DETAILED DESCRIPTION OF THE PREFERRED EMBODIMENT

Figure 1:
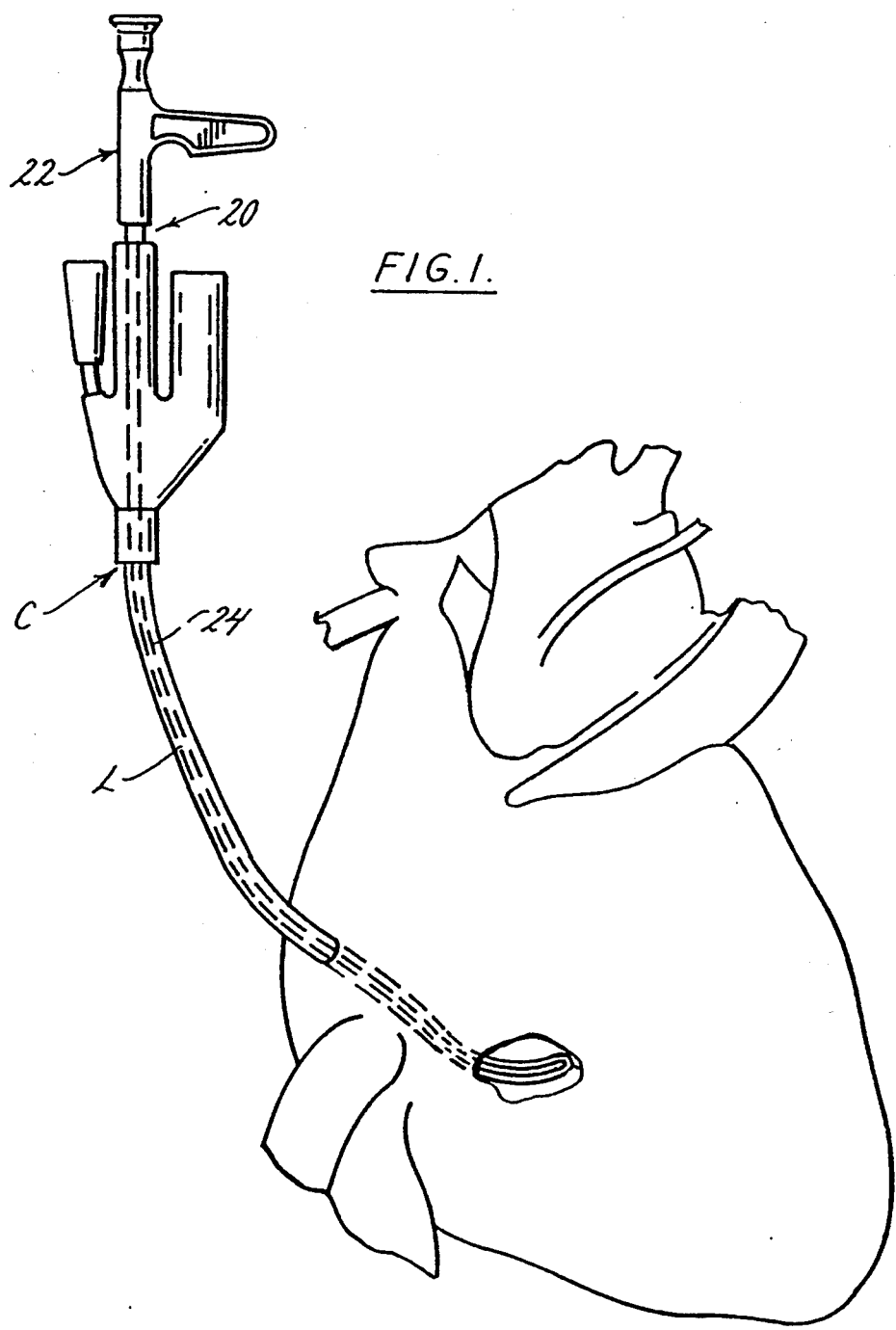
FIG. 1 is a view of a stylet constructed according to the principles of this invention, inserted in the lumen of a coronary cannula, shown as it would be used to manipulate the cannula into the coronary sinus.
Figure 4:
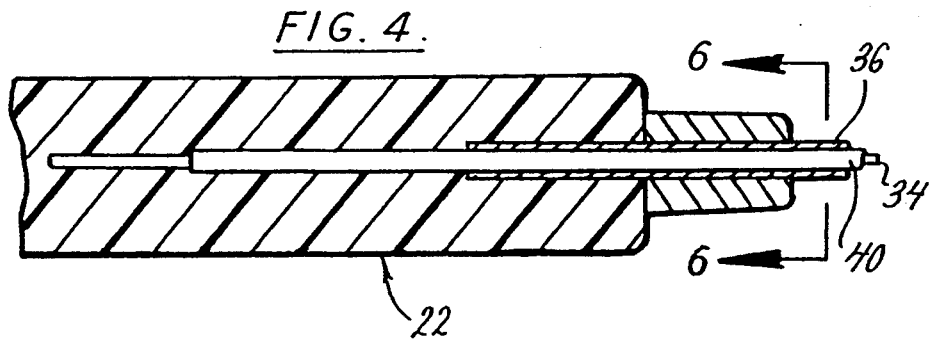
FIG. 4 is an enlarged partial longitudinal cross-sectional view taken along the plane of line 4—4 in FIG. 2.
Figure 5:
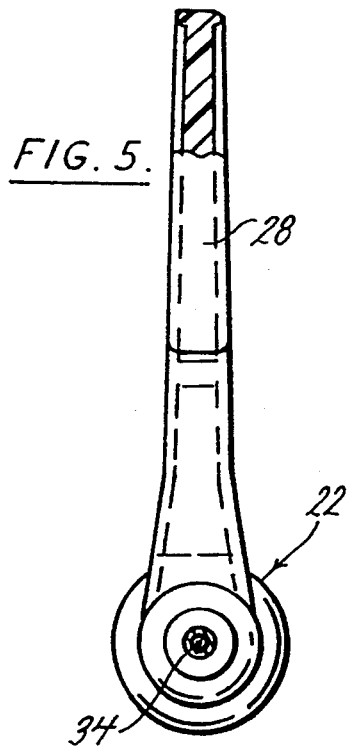
FIG. 5 is a vertical cross-sectional view of the stylet taken along line 5—5 in FIG. 2.
Figure 6:
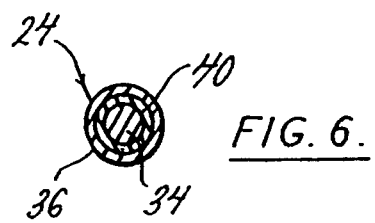
FIG. 6 is a vertical cross-sectional view of the stylet taken along the plane of line 6—6 in FIG. 4.
Figure 3:
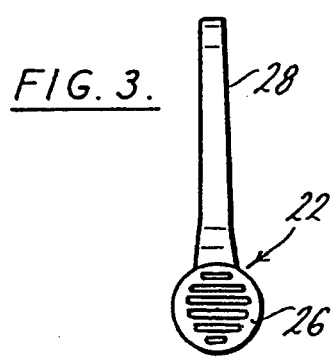
FIG. 3 is an end elevation view of the stylet taken along the plane of line 3—3 in FIG. 2.

A stylet apparatus for installing a coronary cannula in a coronary sinus is indicated generally at 20 in FIGS. 1 and 2. The stylet 20 comprises a handle 22 and a shaft 24 extending from the handle and adapted to fit inside the lumen L of a coronary cannula C. (See FIG. 1). In practice, the coronary cannula C can be provided premounted on the shaft 24 of a stylet 20, to facilitate the proper installation of the cannula C in the coronary sinus. Alternatively the stylet 20 and the cannula C could be provided separately.

The handle 22 of the stylet 20 preferably has a flat base 26, and a finger grip 28, so that the handle 22 can be grasped like a pistol, if desired. Of course some other style of handle could be provided. The handle 22 is preferably made from a molded plastic, such as ABS, although the handle 22 could be made from any other suitable material.

The shaft 24 of the stylet 20 preferably has a stiff but flexible proximal portion 30, and a shorter, malleable distal portion 32. As noted above, the shaft 24 is sized to fit in the lumen L of a coronary cannula C, and is sufficiently long that the distal end of the shaft 24 is closely adjacent to, but does not protrude from, the distal end of the coronary cannula C. (See FIG. 1). The distal portion 32 of the shaft 24 is sufficiently malleable that it can be shaped by hand to a configuration to facilitate the insertion of the cannula C and stylet 20 into the coronary sinus, yet the distal portion 32 is sufficiently stiff to substantially retain this shape as the tip of the cannula C and stylet 20 are manipulated into the coronary sinus. The proximal portion 30 of the shaft 24 is sufficiently stiff to allow the tip of the stylet 20 and cannula C to be steered by manipulating the handle 22. The proximal portion 30 is preferably not so rigid that it cannot be deformed by hand, for example to form a large radius arc in the proximal portion to facilitate installation of the cannula C. The relative lengths of the proximal and distal portions 30 and 32 are important to the steerability of the stylet 20 and cannula C. The distal portion 32 of the stylet 22 must be sufficiently long to hold the shape of the tip of the cannula mounted on the stylet 20. However, the distal portion 32 must be sufficiently short so that the cumulative effect of the flexibility of the distal portion 32 does not unduly interfere with the ability to steer the stylet 20 and cannula C. The distal portion 32 is preferably shorter than the proximal portion 30, and is preferably between 1.5 and 6 inches and most preferably between about 2 and 3 inches (5.1 and 7.6 cm) long. The proximal portion 30 is preferably between about 9 and 10 inches (22.9 and 25.4 cm) long so that the overall length of the shaft 24 is about 12 inches (28.5 cm).

The shaft 24 preferably comprises a long, malleable wire 34 extending from the handle 22. The wire 34 is preferably made of a medical grade stainless steel, such as an SS 303 or SS 304 stainless steel, or other suitable material. The wire is dead soft (annealed), and of sufficient diameter that the wire can be easily shaped by hand into a desired configuration yet hold its shape while the cannula C and stylet 20 are manipulated into the coronary sinus. The wire preferably has a stiffness of between about 0.005 in/in and 0.025 in/in (most preferably 0.01–0.02 in/in (e.g., 0.015 in/in)) as determined by a standard Tenius-Olsen stiffness test with a 30 gram weight at a 0.75 inch deflection. See Federal Military Specification GGN-196 and ASTM D747, incorporated herein by reference, regarding Tenius-Olsen testing. The appropriate diameter may vary, depending on the size of the cannula C and the type of material used. For an SS 303 or 304 stainless steel a diameter of 0.040 inches (0.1016 cm) has been found to be satisfactory. The wire must be sufficiently stiff to retain its shape, but it must be sufficiently flexible to be comfortably manipulated by the surgeon by hand without damaging the cannula C. Also the wire must not be so stiff that it can puncture the tissue surrounding the coronary sinus.

An advantage of the malleable wire is that for a given tip sharpness, the greater the flexibility, the greater force required to penetrate a given structure, for example the wall of the coronary sinus. Penetration pressure can be measured using an Instron Stress Machine to push a test piece through a standard medium, such as a 3 mm or 5 mm thick polyethylene sheet. The inventors conducted such tests measuring the puncture pressure at 3 inches from the tip when formed in a "C" and 6 inches from the tip and found that the average puncture pressure for ten repetitions is significantly higher with inventors' compound stylet 20. This means that greater force can be applied to the inventors' stylet 20 without puncturing the heart tissue.

The proximal portion of the wire 34 (i.e., the portion adjacent the handle 22) is surrounded by a tubular sheath 36. The sheath 36 stiffens the proximal portion of the wire, forming the relatively stiff proximal portion 30 of the shaft 24. For a wire diameter of about 0.040 inches (0.1016 cm), the sheath 36 can be a 14 gauge stainless steel tube. Of course, with different wire diameters, different tube gauges can be used. The section of the wire 34 covered by the sheath 36 forms the stiff but flexible proximal portion 30. The compound construction with the wire 34 extending through the sheath 36 prevents the proximal portion 30 from kinking. The distal portion 32 of the wire 34 protruding from the sheath 36 forms the malleable distal portion 32 of the shaft. The compound construction of the shaft 24 is relatively simple and inexpensive to manufacture. The fact that the wire 34 extends the length of the shaft 24 reduces the risk that the distal portion 32 will break off or separate from the shaft 24.

The wire 34 preferably has a coating 40, which may be a nylon, such as "ZYTEL 408 TM " nylon resin, or other suitable plastic. "ZYTEL 408 TM " is a trademark used in connection with a nylon resin available from E. I. Du Pont De Nemours & Company, Wilmington, Del. The coating 40 is preferably colored so that it is visible through the walls of the cannula C in which it is placed. The color of the coating 40 provides an indication of the depth of penetration of the tips of the cannula C and stylet 20 into the heart atrium, which helps to indicate when the tip of the cannula C is properly placed. At the point where the colored coating is no longer visible, the surgeon knows that the tips of the cannula C and stylet 20 are at a depth corresponding to the length of the proximal portion 30. This helps the surgeon to avoid inserting the cannula C past the coronary sinus, and possibly damaging the heart.

The entire stylet 20 is preferably coated with a silicone-based lubricant to facilitate the removal of the stylet 20 after the cannula C is properly placed in the coronary sinus. The lubricant allows the stylet 20 to be withdrawn without pulling the coronary cannula C from the heart. The coating 40 also facilitates the removal of the deformed distal portion 32 from the cannula C with a minimum of disruption.

OPERATION

A coronary cannula C is preferably provided in a sterile package, already mounted on the shaft 24 of a stylet 20. The surgeon bends the tip of the cannula C, deforming the distal portion 32 of the shaft 24, to the desired configuration to facilitate the installation of the cannula C in the coronary sinus. The distal portion 32 deforms to hold the end of the coronary cannula C in the desired shape. An incision is made in the right atrium, and the coronary cannula C and stylet 20 are manipulated to bring the tip of the cannula C into the coronary sinus. The amount of colored coating 40 that is visible through the wall of the cannula C indicates to the surgeon the depth of the cannula tip in the heart. When the coronary cannula C is properly placed in the coronary sinus, it is anchored by means known in the art, for example, by inflating a balloon provided on the cannula C for that purpose. Once the coronary cannula C is firmly anchored, the stylet 20 is removed from the cannula C. The lubricant coating facilitates the removal of the stylet 20 from the coronary cannula C with a minimum of disruption to the cannula C.

As various changes could be made in the above constructions without departing from the scope of the invention, it is intended that all matter contained in the above description or shown in the accompanying drawings shall be interpreted as illustrative and not in a limiting sense.

What is claimed is:

1. A stylet adapted to fit inside a retrograde coronary cannula to facilitate the installation of the cannula into the coronary sinus, the stylet comprising:
   a handle;
   a shaft extending from the handle and adapted to fit inside the coronary cannula, the shaft comprising;
   a generally elongate proximal portion means for providing stiffness to a proximal portion of the cannula in which the stylet is received; and
   a generally elongate, deformable distal portion means, shorter than the proximal portion means and extending distally from the proximal portion means, for providing stiffness to a distal portion of the cannula in which the stylet is received, the deformable distal portion means including deformable means, readily deformable in comparison with the proximal portion means, for holding the distal tip of the coronary cannula in a desired configuration in which the distal portion means has been deformed to facilitate the insertion of the cannula into the coronary sinus;
   the proximal portion means being relatively stiff in comparison with the deformable distal portion means.

2. The stylet according to claim 1 wherein the shaft comprises a malleable wire forming the deformable means of the distal portion means.

3. The stylet according to claim 2 wherein the wire is an annealed stainless steel.

4. The stylet according to claim 2 wherein the wire has a Tenius-Olsen stiffness of between about 0.005 in/in and about 0.025 in/in.

5. The stylet according to claim 2 wherein the malleable wire includes a distal portion forming the distal portion means and a proximal portion extending proximally of the distal portion; the proximal portion means comprising the proximal portion of the wire, and a sleeve surrounding the proximal portion of the wire, stiffening the proximal portion means of the shaft, the sleeve being relatively rigid in comparison with the malleable wire, thereby making the proximal portion means less readily deformable than the distal portion means.

6. The stylet according to claim 1 wherein the deformable distal portion means has a length of between about 1.5 and about 6 inches, and the proximal portion means has a length of between about 9 and about 10 inches.

7. A coronary cannula and installation stylet set comprising:
   a retrograde coronary sinus cannula having a lumen and defining proximal and distal directions; and
   an installation stylet comprising;
   a handle defining a proximal end of the stylet; and
   a shaft extending distally from the handle and extending through the lumen of the coronary cannula, the shaft comprising;
   a generally elongate proximal portion means for providing stiffness to a proximal portion of the cannula in which the stylet is received; and
   a generally elongate, deformable distal portion means, shorter than the proximal portion means and extending distally from the proximal portion means, for providing stiffness to a distal portion of the cannula in which the stylet is received, the deformable distal portion means including deformable means, readily deformable in comparison with the proximal portion means, for holding the distal tip of the coronary cannula in a desired configuration in which the distal portion means has been deformed to facilitate the insertion of the cannula into the coronary sinus
   the proximal portion means being relatively stiff in comparison with the distal portion means.

8. The coronary cannula and stylet set according to claim 7 wherein the shaft comprises a malleable wire forming the deformable means of the distal portion means.

9. The coronary cannula and stylet set according to claim 8 wherein the wire is an annealed stainless steel.

10. The coronary cannula and stylet set according to claim 8 wherein the wire has a Tenius-Olsen stiffness of between about 0.005 in/in and about 0.025 in/in.

11. The coronary cannula and stylet set according to claim 8 wherein the malleable wire includes a distal portion forming the distal portion means and a proximal portion extending proximally of the distal portion; the proximal portion means comprising a sleeve surrounding the proximal portion of the wire, stiffening the proximal portion means of the shaft, the sleeve being relatively rigid in comparison with the malleable wire, thereby making the proximal portion means less readily deformable than the distal portion means.

12. The coronary cannula and stylet set according to claim 8 wherein the deformable distal portion means has a length of between about 1.5 and about 6 inches, and the proximal portion means has a length of between about 9 and about 10 inches.

13. A method of installing a retrograde coronary cannula in the coronary sinus, the method comprising the steps of:
   providing a coronary cannula having a lumen and defining proximal and distal ends and a tip portion adjacent the distal end, and a stylet having a shaft extending through the lumen of the cannula, the shaft having a proximal portion, and a deformable distal portion shorter and more readily deformable than the proximal portion, the shaft being sufficiently long that the deformable distal portion extends within the lumen of the cannula generally to the tip of the coronary cannula, with the proximal portion of the shaft received within the lumen of the cannula;

inserting the stylet into the lumen of the cannula such that the distal and proximal portions of the shaft of the stylet are received in the lumen of the cannula;

either before or after the step of inserting the stylet into the lumen of the cannula, deforming the deformable distal portion of the stylet in order to shape the tip of the cannula into which the stylet shaft is inserted either before or after this step, thereby to facilitate insertion of the cannula into the coronary sinus;

manipulating the tip portion of the coronary cannula into the coronary sinus; and removing the stylet from the coronary cannula when the coronary cannula is in place in the coronary sinus.

14. The method of installing a retrograde coronary cannula according to claim 13 wherein the deformable distal portion of the stylet shaft comprises a malleable wire between about 1.5 and about 6 inches long, the step of deforming the distal portion of the stylet shaft further comprising deforming the malleable wire.

15. The method of installing a retrograde coronary cannula according to claim 13 wherein the deformable distal portion of the stylet shaft comprises a malleable wire having a Tenius-Olsen stiffness of between about 0.005 in/in and about 0.025 in/in; the step of deforming the distal portion of the stylet shaft further comprising deforming the malleable wire.

16. A method of installing a retrograde coronary cannula in the coronary sinus, the method comprising the steps of:

providing a coronary cannula with the shaft of a stylet extending through the lumen of the cannula, the shaft comprising a deformable wire and a tube extending over the proximal portion of the wire to make the proximal portion of the shaft stiff but flexible, with the wire protruding from the tube and forming a deformable distal portion comprising less than half the length of the shaft, the shaft being sufficiently long that the deformable distal portion extends generally to the tip of the coronary cannula;

shaping the tip of the coronary cannula by deforming the deformable distal portion of the stylet therein to facilitate its insertion into the coronary sinus;

manipulating the tip of the coronary cannula into the coronary sinus; and removing the stylet from the coronary cannula when the coronary cannula is in place in the coronary sinus.

17. The method of installing a coronary cannula according to claim 16 wherein the deformable distal portion of the stylet is between about 1.5 and about 6 inches long.

18. The method of installing a retrograde coronary cannula according to claim 16 wherein the deformable distal portion of the stylet shaft has a Tenius-Olsen stiffness of between about 0.005 in/in and about 0.025 in/in.

19. A coronary cannula and installation stylet set comprising:

a retrograde coronary sinus cannula having a lumen and defining proximal and distal ends and a tip portion generally adjacent the distal end; and an installation stylet comprising:
a handle defining a proximal end of the stylet; and
a generally elongate shaft extending distally from the handle and extending substantially through the lumen of the coronary cannula, the shaft comprising:

a generally elongate malleable wire having proximal and distal portions; and a generally elongate sleeve surrounding the proximal portion of the malleable wire, the sleeve having a length longer than the length of the distal portion of the malleable wire and being relatively stiff in comparison with the malleable wire to provide stiffness to a proximal portion of the cannula;

the distal portion of the malleable wire extending distally from the sleeve, the distal portion of the malleable wire being readily deformable in comparison with the sleeve, thereby facilitating deforming the malleable wire to hold the distal tip of the coronary cannula in a desired configuration to facilitate the insertion of the cannula into the coronary sinus.

20. The coronary cannula and stylet set according to claim 19 wherein the malleable wire is an annealed stainless steel, the malleable wire having a Tenius-Olsen stiffness of between about 0.005 in/in and about 0.025 in/in.

21. The coronary cannula and stylet set according to claim 19 wherein the deformable distal portion of the malleable wire has a length of between about 1.5 and about 6 inches, and the sleeve has a length of between about 9 and about 10 inches.

* * * * *

UNITED STATES PATENT AND TRADEMARK OFFICE
CERTIFICATE OF CORRECTION

PATENT NO. : 5,401,244
DATED : March 28, 1995
INVENTOR(S) : Christopher M. Boykin and Thomas T. Vaalburg It is certified that error appears in the above-indentified patent and that said Letters Patent is hereby corrected as shown below: On the title page:

Under section [56] "References Cited" add the following:

5,344,399  9/1994  DeVries.....604/96
    0620022   10/1994  European Pat. Off....A61M 25/01

Signed and Sealed this

Twenty-fourth Day of October, 1995

Attest:

BRUCE LEHMAN

*Attesting Officer*   *Commissioner of Patents and Trademarks*